(12) United States Patent
Hiramura et al.

(10) Patent No.: US 10,828,257 B2
(45) Date of Patent: *Nov. 10, 2020

(54) DISINTEGRATING PARTICLE COMPOSITION INCLUDING MICROFIBROUS CELLULOSE

(71) Applicant: Daicel Corporation, Osaka (JP)

(72) Inventors: Takahiro Hiramura, Tokyo (JP); Kiyoshi Ikura, Himeji (JP); Sae Itaya, Himeji (JP); Tomohito Okabayashi, Himeji (JP); Yoshihisa Takigawa, Himeji (JP); Anan Sakaguchi, Himeji (JP); Naohiro Hashikawa, Himeji (JP)

(73) Assignee: DAICEL CORPORATION, Osaka (JP)

( * ) Notice: Subject to any disclaimer, the term of this patent is extended or adjusted under 35 U.S.C. 154(b) by 96 days.

This patent is subject to a terminal disclaimer.

(21) Appl. No.: 15/127,719

(22) PCT Filed: Apr. 7, 2015

(86) PCT No.: PCT/JP2015/060799
§ 371 (c)(1),
(2) Date: Sep. 20, 2016

(87) PCT Pub. No.: WO2015/163135
PCT Pub. Date: Oct. 29, 2015

(65) Prior Publication Data
US 2018/0214377 A1  Aug. 2, 2018

(30) Foreign Application Priority Data

Apr. 21, 2014  (JP) .................................. 2014-087642
Nov. 17, 2014  (JP) .................................. 2014-233159

(51) Int. Cl.
| | |
|---|---|
| A61K 9/16 | (2006.01) |
| A61K 9/20 | (2006.01) |
| A61K 47/32 | (2006.01) |
| A61K 47/38 | (2006.01) |
| A61K 47/26 | (2006.01) |
| A61K 47/10 | (2017.01) |
| A61K 47/36 | (2006.01) |

(52) U.S. Cl.
CPC .............. *A61K 9/1652* (2013.01); *A61K 9/16* (2013.01); *A61K 9/1623* (2013.01); *A61K 9/20* (2013.01); *A61K 9/2018* (2013.01); *A61K 9/2054* (2013.01); *A61K 9/2059* (2013.01); *A61K 47/10* (2013.01); *A61K 47/26* (2013.01); *A61K 47/32* (2013.01); *A61K 47/36* (2013.01); *A61K 47/38* (2013.01)

(58) Field of Classification Search
CPC ........ A61K 47/10; A61K 47/26; A61K 47/32; A61K 47/36; A61K 47/38; A61K 9/16; A61K 9/1623; A61K 9/1652; A61K 9/20; A61K 9/2018; A61K 9/2054; A61K 9/2059

See application file for complete search history.

(56) References Cited

U.S. PATENT DOCUMENTS

| | | | |
|---|---|---|---|
| 4,374,702 A | 2/1983 | Turbak et al. | |
| 4,483,743 A | 11/1984 | Turbak et al. | |
| 6,214,163 B1* | 4/2001 | Matsuda | ................ D21C 9/007 |
| | | | 162/100 |
| 2002/0061335 A1 | 5/2002 | Kumar | |
| 2011/0053942 A1 | 3/2011 | Fujiwara | |
| 2011/0150989 A1 | 6/2011 | Park et al. | |
| 2012/0214979 A1 | 8/2012 | Heiskanen et al. | |
| 2012/0309898 A1* | 12/2012 | Hamada | .................. C08B 15/05 |
| | | | 525/54.23 |

FOREIGN PATENT DOCUMENTS

| | | | | |
|---|---|---|---|---|
| EP | 1 980 272 | 10/2008 | | |
| EP | 2 251 005 | 11/2010 | | |
| EP | 2 368 544 | 9/2011 | | |
| EP | 2 465 495 | 6/2012 | | |
| JP | S56100801 | 8/1981 | | |
| JP | S61236731 | 10/1986 | | |
| JP | S63301820 | 12/1988 | | |
| JP | 10-182436 | 7/1998 | | |
| JP | 2000-273039 | 10/2000 | | |
| JP | 2000513727 | 10/2000 | | |
| JP | 2001086957 | 4/2001 | | |
| JP | 2002-179558 | 6/2002 | | |
| JP | 2000-273039 | * 10/2003 | ............. | A61K 47/10 |
| JP | 2004283135 | 10/2004 | | |
| JP | 2006160627 | 6/2006 | | |
| JP | 2006290972 | 10/2006 | | |

(Continued)

OTHER PUBLICATIONS

International Search Report of International Application No. PCT/JP2015/060799 dated Jul. 7, 2015.

(Continued)

*Primary Examiner* — Matthew P Coughlin
*Assistant Examiner* — Thurman Wheeler
(74) *Attorney, Agent, or Firm* — Ping Wang; Morris, Manning & Martin LLP

(57) ABSTRACT

The purpose of the present invention is to provide a disintegrating tablet having excellent tablet hardness and disintegrability, which is suitable for pharmaceuticals and various kinds of foods such as supplemental foods, nutrition function foods and health foods has been desired as highly convenient forms which can safely be taken by patients who have difficulty in swallowing drugs, elderly people, children, etc., and which can easily be taken without water irrespective of places; and a disintegrative particulate composition comprised in the disintegrating tablet.

The present invention relates to a disintegrative particulate composition comprising a disintegrator component and micro-fibrillated cellulose, and a disintegrating tablet for pharmaceuticals or foods, comprising the disintegrative particulate composition, which has excellent tablet hardness and disintegrability.

13 Claims, No Drawings

(56) References Cited

FOREIGN PATENT DOCUMENTS

| | | |
|---|---|---|
| JP | 2007-153887 | 6/2007 |
| JP | 2007-231438 | 9/2007 |
| JP | 2008-285434 | 11/2008 |
| JP | 2009203559 | 9/2009 |
| JP | 2010-529074 | 8/2010 |
| JP | 4551627 | 9/2010 |
| JP | 2012-031138 | 2/2012 |
| JP | 2013-147470 | 8/2013 |
| WO | 2004108164 | 12/2004 |
| WO | 2009/102038 | 8/2009 |
| WO | 2011/019043 | 2/2011 |
| WO | 2011/019045 | 2/2011 |
| WO | 2012/087377 | 6/2012 |
| WO | 2013/146917 | 10/2013 |

OTHER PUBLICATIONS

Kolakovic, R. et al., "Spray-Dried Cellulose Nanofibers as Novel Tablet Excipient," AAPS PharmSciTech, Dec. 2011, vol. 12, Issue 4, pp. 1366-1373.

* cited by examiner

DISINTEGRATING PARTICLE COMPOSITION INCLUDING MICROFIBROUS CELLULOSE

FIELD

The present invention relates to a disintegrative particulate composition comprising micro-fibrillated cellulose, and to various kinds of disintegrating tablets comprising said composition.

BACKGROUND ART

Cellulose that is produced from a vegetable fiber and having a fiber diameter (a short diameter) or thickness of from about a few nm to a few μm has been generally known as "fine-fibrillated cellulose" or "micro-fibrillated cellulose." The production examples and its structure, properties and functions are described in Patent Literature (PTL) 1 and PTL 2 cited below.

In the fine- or micro-fibrillated cellulose, a surface area has been increased, hydrophilic property that is the original characteristics of cellulose has been significantly strengthened, and a three-dimensional network has been formed, without deteriorating basic properties such as physical and chemical stabilities of a starting material of cellulose. As a result, when it is formulated into goods in a paste or cream shape, it will show a water-retaining (syneresis-preventing) property and a form-retaining property due to the interaction with water and oil droplets, fine particles, etc. It is also utilized to modify goods in a jelly form, for example, to increase their strength.

Accordingly, the above cellulose has been widely used in various applications, for example, as a binder for powder and fibrous materials, a paper strong agent in papermaking, a thickening agent for improving food texture of foods, a humectant for water-retaining of foods, a filter aid for alcoholic beverage and the like.

As an application example of the micro-fibrillated cellulose, PTL 3 describes a gelly composition comprising a water-dispersible complex comprising the micro-fibrillated cellulose and a hydrophilic polymer that is soluble in warm water in a particular ratio; a gelling agent; and water in a particular ratio. It describes that the composition has properties to inhibit denaturation of proteins and precipitation of water-insoluble components during heating or warming treatment and to give a good food texture.

PTL 4 describes a gelling agent comprising a highly dispersible cellulose complex comprising the micro-fibrillated cellulose, a water-soluble polymer and hydrophilic substance in a particular ratio; and a particular kind of polysaccharide in a particular ratio. It describes that the agent is characterized as being superior in disintegration and dispersion in water when compared to a conventional highly dispersible cellulose complex, so that it can be used in industrial and practical dispersing conditions.

Thus, the micro-fibrillated cellulose is used as a one component in the gelly composition and gelling agent disclosed in PTL 3 and 4. Furthermore, the hydrophilic polymer is an essential component for the water-dispersible complex of PTL 3, and the water-soluble polymer is an essential component for the highly dispersible cellulose complex of PTL 4.

RELATED ARTS

Patent Literatures

PTL 1: JP-A-Sho 56-100801
PTL 2: JP-A-2009-203559
PTL 3: JP-A-2004-283135
PTL 4: JP-A-2006-290972

SUMMARY

Problems to be Solved by the Invention

The prior arts disclose no example of a disintegrative particulate composition utilizing excellent properties of the micro-fibrillated cellulose, and various kinds of disintegrating tablets comprising the composition. A disintegrating tablet for pharmaceuticals and various kinds of foods such as supplemental foods, nutrition function foods and health foods has been desired as highly convenient forms that can be safely taken by patients who have difficulty in swallowing drugs, elderly people, children, etc., and can be easily taken without water irrespective of places.

Accordingly, an object of the present invention is to solve such technical problems as mentioned above, and to provide a disintegrative particulate composition comprising the micro-fibrillated cellulose, and various kinds of disintegrating tablets comprising said composition for pharmaceuticals and various kinds of foods.

Means to Solve the Problem

The present inventors have earnestly studied and found unexpected advantages that by adding the micro-fibrillated cellulose to the composition conventionally used as a disintegrator, tablet hardness of the various kinds of disintegrating tablets comprising said composition shall be increased while disintegration time in water shall be shortened due to a synergistic effect of the conventional composition and micro-fibrillated cellulose.

Thus, the present invention relates to the following aspects.

Aspect 1
A disintegrative particulate composition comprising a disintegrator component and micro-fibrillated cellulose.

Aspect 2
The disintegrative particulate composition according to Aspect 1, wherein the micro-fibrillated cellulose has an average fiber length of 0.01~2 mm and an average fiber diameter of 0.001~1 μm.

Aspect 3
The disintegrative particulate composition according to Aspect 1 or 2, wherein the disintegrator is one or more components selected from crospovidone, croscarmellose sodium, low substituted hydroxypropylcellulose, carboxymethylcellulose calcium, starch and processed starch.

Aspect 4
The disintegrative particulate composition according to Aspect 3, wherein the starch is corn starch, potato starch, waxy corn starch, α-starch or partially α-starch, and the processed starch is starch sodium glycolate or hydroxypropyl starch.

Aspect 5
The disintegrative particulate composition according to any one of Aspects 1-3, wherein the disintegrator is a water-insoluble polymer.

Aspect 6
The disintegrative particulate composition according to any one of Aspects 1-5, further comprising sugars or sugar alcohols.

Aspect 7

The disintegrative particulate composition according to any one of Aspects 1-6, further comprising an auxiliary excipient.

Aspect 8

The disintegrative particulate composition according to Aspect 7, wherein the auxiliary excipient is a crystalline cellulose and/or powdered cellulose.

Aspect 9

A disintegrating tablet for pharmaceuticals or foods, comprising the disintegrative particulate composition according to any one of Aspects 1-8.

Aspect 10

The disintegrating tablet according to Aspect 9, which has tablet hardness of from 20 to 200 N, and disintegration time in water of from 1 to 60 sec.

Advantages of Invention

Due to the synergistic effect by the micro-fibrillated cellulose and disintegrator component added to the disintegrative particulate composition, the various kinds of disintegrating tablets are provided with excellent tablet hardness and disintegrability that are desired for them, and with an excellent formability in the production of the tablets.

DESCRIPTION OF EMBODIMENTS OF THE INVENTION

The present invention relates to the disintegrative particulate composition comprising the disintegrator component and micro-fibrillated cellulose. Any cellulose conventionally known as the "fine-fibrillated cellulose" or "micro-fibrillated cellulose" can be used as the "micro-fibrillated cellulose" in the present invention.

As already mentioned, the micro-fibrillated cellulose is generally produced from the vegetable fiber and having the fiber diameter (the short diameter) or thickness of from about a few nm to 1 µm. The surface area of the micro-fibrillated cellulose has been increased, its hydrophilic property that is the original characteristics of cellulose has been significantly strengthened, and its three-dimensional network has been formed, without deteriorating the basic properties such physical and chemical stabilities of the starting material of cellulose.

A dry material of the micro-fibrillated cellulose may be directly obtained in a dry state by any method known in the art, such as by directly pulverizing cellulose fiber in a dry state with a ball mill (PTL 1). Alternatively, the dry material of the micro-fibrillated cellulose may be obtained by subjecting the micro-fibrillated cellulose suspended in water, which was prepared by micro-fibrillation of water-dispersion of the cellulose fiber with a high-pressure homogenizer, to a solvent displacement stage, and removing the solvent in a drying stage, followed by pulverization in a pulverizing stage (PTL 2).

Preferable examples of the micro-fibrillated cellulose comprised in the disintegrative particulate composition according to the present invention include fiber assembly that has an average fiber length of 0.01~2 mm and an average fiber diameter of 0.001~1 µm, preferably of 0.01~0.1 µm (PTL 2). For example, such micro-fibrillated cellulose is commercially available with a trade name of "CELISH" series (a solid content of 10~35% in water) with various grades (an average fiber diameter of 0.01~0.1 µm) from Daicel FineChem Ltd.

As the disintegrator component comprised in the disintegrative particulate composition of the present invention, any disintegrators known to a person skilled in the art, can be used. For example, it may comprise one or more components selected from crospovidone, croscarmellose sodium, low substituted hydroxypropylcellulose, carboxymethylcellulose calcium, starch such as corn starch, potato starch, waxy corn starch, α-starch or partially α-starch, and processed starch such as starch sodium glycolate and hydroxypropyl starch. Additionally, crospovidone is a common name for a cross-linked polymer of 1-vinyl-2-pyrrolidone, and croscarmellose sodium is a common name for a cross-linked product of carboxymethylcellulose sodium.

Among the above disintegrator components, crospovidone, croscarmellose sodium, low substituted hydroxypropylcellulose, carboxymethylcellulose calcium and the like are water-insoluble polymers. The starch such as corn starch, potato starch, waxy corn starch, water-insoluble α-starch or water-insoluble partially α-starch; and the processed starch such as starch sodium glycolate and hydroxypropyl starch are also water-insoluble polymers.

The disintegrative particulate composition according to the present invention may further comprise any sugars or sugar alcohols known in the art as an excipient.

The sugars or sugar alcohols include mannitol, erythritol, xylitol, trehalose, lactose, maltose, maltitol, glucose, sucrose, fructose, mannose, and sorbitol. Moreover, as preferable examples thereof, mannitol, erythritol, xylitol, trehalose, and lactose can be mentioned. As the sugars or sugar alcohols, two or more types of compounds properly selected from these compounds can also be used.

Furthermore, the disintegrating tablet can be provided with more excellent tablet hardness and disintegrability by having the auxiliary excipient such as crystalline cellulose and/or powdered cellulose comprised in the disintegrative particulate composition according to the present invention. The crystalline cellulose is a white water-insoluble powdery substance obtained by partially depolymerizing α-cellulose, which is obtained from fibrous plants, with acids, followed by purification. The crystalline cellulose has no taste, and, since the substance is chemically inactive, it does not change even when being mixed with medicaments. Therefore, the crystalline cellulose has been used for purposes of a pharmaceutical additive, in particular, an auxiliary excipient, binder, disintegrator or the like for preparing tablets. In addition, the crystalline cellulose has been used as an emulsification stabilizer or the like for cosmetics, dairy products, etc. besides an additive for pharmaceuticals.

Any crystalline cellulose and/or powdered cellulose known in the art can be used. As typical examples of the crystalline cellulose, commercially-available products such as "Avicel" (FMC Corporation), "CEOLUS" (Asahi Kasei Chemicals Corp.), and "VIVAPUR" (RETTENMAIER) can be mentioned. As typical examples of the powdered cellulose, commercially-available products such as KC Flock (NIPPON PAPER Chemicals CO., LTD) and ARBOCEL (RETTENMAIER) and Solka Flock (Kimura Sangyo Co., Ltd.)

An amount of each component comprised in the disintegrative particulate composition of the present invention can properly be determined by a person skilled in the art, depending on, for example, the type of the component, the type and purpose of the disintegrating tablet, which is a target to be used for the disintegrative particulate composition. In general, relative to the total weight of the disintegrative particulate composition, the amount of the micro-fibrillated cellulose (in terms of a dry weight) is within a range of 1% to 50% by weight, the amount of the disintegrator component is within a range of 1% to 30% by weight, the amount of the sugars or sugar alcohols, if present, is within a range of 20% to 98% by weight, and the auxiliary excipient such as crystalline cellulose and/or powdered cellulose is within a range of 1% to 40% by weight.

In addition, these physical properties are measured by using the following methods and conditions.

The average particle size: 2 g of the disintegrative particulate composition is subjected to a measurement with a Φ75 mm automatic shaking sieve device (Type "M-2", Tsutsui Scientific Instruments Co., Ltd.).

The water content: 5 g of the disintegrative particulate composition is subjected to a measurement using a halogen water content measuring device (Type "HB43", METTLER TOLEDO K.K.).

Furthermore, in addition to the above-described components, various types of optional components known to a person skilled in the art may properly be added and mixed into the disintegrative particulate composition of the present invention, for the purpose of adjusting various characteristics such as the disintegrating force, binding force and ease in taking the tablet, without impairing the effects of the present invention by the above-described components. As examples of such components, disintegrators, auxiliary excipients, fluidizing agents, sweetening agents, corrigents, flavoring agents and coloring agents can be mentioned.

Starch and inorganic excipients may be used as the disintegrators and auxiliary excipients, respectively. Examples of the starch include corn starch, potato starch, waxy corn starch, α-starch or partially α-starch. Examples of the inorganic excipients include light anhydrous silicic acid, silicon dioxide hydrate, anhydrous calcium phosphate, anhydrous calcium hydrogenphosphate, aluminum metasilicate, calcium silicate, magnesium oxide.

The disintegrative particulate composition according to the present invention may be produced by any method or means known to a person skilled in the art.

For examples, the disintegrative particulate composition according to the present invention may be produced by mixing each of the components comprised in the composition all together.

Alternatively, it may be produced by various granulation processes. Any granulation method may be used, and a dry granulation process and a wet granulation process may be used to produce the composition.

The dry granulation process comprises the steps of mixing each powder of the components comprised in the disintegrative particulate composition optionally with an appropriate binder and the like, breaking the resulting mixture into small bulks with a high pressure, and appropriately crushing and granulating them. Examples of the dry granulation process include crushing granulation and roll-compressing method.

The wet granulation process is a method in which each component is dispersed in the presence of water, and the dispersion is dried to form complexes. As specific examples of the wet granulation process, spray methods such as spray drying, tumbling granulation, agitation granulation and fluidized-bed granulation; the freeze-drying method; kneading granulation, and the like can be mentioned, and the composition can be produced by any of these methods known to a person skilled in the art.

The disintegrative particulate composition according to the present invention may be produced by one wet granulation step using all of the components comprised therein together, or by adding and mixing each component in the plural wet granulation steps.

A person skilled in the art can properly determine which one or two types of the components comprised in the disintegrative particulate composition in the above plural wet granulation steps, depending on their types, amounts, etc.

Furthermore, a person skilled in the art can properly determine various conditions in the above plural wet granulation steps, such as the spraying speed, the supply air temperature, the exhaust temperature, and the air supply rate, depending on types or amounts of components, etc.

In each of the above granulation step, as a medium for the spray liquid, a solvent acceptable in pharmaceuticals or foods, such as water, ethanol, methanol or acetone, can be mentioned. Alternatively, as the spray liquid, for example, an aqueous solution in which less than 10% of the component(s) for the disintegrative particulate composition is dissolved can be mentioned, and, in particular, water or such an aqueous solution is preferable.

As shown in Example 6, for example, the disintegrative particulate composition according to the present invention may be produced by means of spraying dispersion liquid (slurry) of the micro-fibrillated cellulose into a fluidized-bed granulator containing all the components of the composition except the micro-fibrillated cellulose.

Each of the above components that may be optionally comprised in the disintegrative particulate composition according to the present invention may be optionally added in any of the above granulation steps. Alternatively, the above optional components may be added and mixed in an additionally-provided wet granulation step.

It is preferable that the disintegrative particulate composition of the present invention produced by the above wet granulation process has the following physical properties:
(1) an average particle size of 50 to 200 microns; and
(2) a water content of 0.5% to 6% by weight, e.g. 0.5% to 7% by weight.

The present invention also relates to a disintegrating tablet comprising the above disintegrative particulate composition, especially to an orally disintegrating tablet for pharmaceuticals or foods such as supplemental foods, nutrition function foods and health foods. The content of the disintegrative particulate composition in the disintegrating tablet can properly be determined by a person skilled in the art, depending on, for example, the application and purpose of the disintegrating tablet, without impairing the effects of the present invention. There is no particular limitation on the shape or form of the tablet.

The disintegrating tablet has the excellent tablet hardness and disintegrability since it comprises the disintegrative particulate composition of the present invention. As shown by the examples, it is characterized by having a hardness of 20 to 200 N, preferably 30 to 150 N, more preferably 50 to 150 (N), and by having a disintegration time in water of 1 to 60 seconds, preferably 1 to 45 seconds, more preferably 1 to 30 seconds, when it is produced at tablet compression forces of 2 to 30 kN.

The disintegrating tablet according to the present invention may optionally comprise any other components than the disintegrative particulate composition.

The disintegrating tablet for foods may optionally comprise, for example, various nutritional components such as proteins, carbohydrates, lipids and minerals; various vitamins and their derivatives; and designated or existing additives according to Food Sanitation Law, Art. 10; and other components acceptable as a food component (a food additive) listed in a list of general additives for food and drink, such as acidulants, sweeteners, excipients, surfactants, lubricants, corrigents, flavoring agents, colorants, and stabilizing agents, The orally disintegrating tablet for pharmaceuticals may optionally comprise, for example, in addition to a medicinal ingredient and said disintegrative particulate composition, other components acceptable as additives from a pharmaceutical or food-sanitary point of view, such as excipients, surfactants, lubricants, acidulants, sweeteners, corrigents, flavoring agents, colorants, and stabilizing agents, when needed. As these optional components, for example, appropriate ingredients described in "Japanese Pharmaceutical Excipients Directory" (YAKUJI NIPPO LIMITED) or the Japanese Pharmacopoeia; designated or existing additives according to Food Sanitation Law, Art. 10; natural flavor; and additives listed in a list of general additives for food and drink can be used. There is no limitation in the kind of the medicinal ingredient and the above auxiliary agents. Also, the blending ratios of the disintegrative particulate composition, the medicinal ingredient and each optional ingredient (component) are not particularly limited as long as the expected effects of the present invention are brought about, and the blending ratios can properly be determined by those skilled in the art. The orally disintegrating tablet can be formulated by any methods known to those skilled in the art, for example, by tableting. There is no limitation on an application or kind of the medicinal ingredients comprised in the orally disintegrating tablet according to the present invention, which may include, for example, agents affecting each organ such as the central nervous system, peripheral nervous system, a sensory organ, a circulatory organ, a respiratory organ and a digestive organ and an urogenital organ; hormone drug; agents affecting metabolism such as a vitamin drug, an analeptic, an agent affecting blood and body fluid; agents affecting the function of tissue and cell such as an agent activating cellular function, an agent affecting tumors, an radioactive medicine, an anti-allergic agent; medicines based on a medical prescription relating to herbal medicines and Chinese medicines; antibiotics; agents for chemotherapy, biological drug; agents for pathogenic organisms such as parasites; agents for formulation use, diagnosis, public health and in-vitro diagnosis.

In addition, contents of all related art documents cited in the present specification are incorporated herein by reference.

Hereinafter, the present invention will more specifically be described with reference to Examples. However, the present invention is not considered to be limited to the Examples.

Evaluation on Hardness and Disintegrability Tests

Values of the physical properties of the tablets obtained in the Examples were measured based on the following conditions/methods. The test results of hardness and disintegration time are shown in Tables 1-5 below.

Hardness: a hardness (N) was measured with a digital Kiya hardness tester (Fujiwara Scientific Company Co., Ltd.).

Disintegration time in water: a disintegration time in water was measured with a disintegration tester (NT-400, TOYAMA SANGYO CO., LTD.) in accordance with the method described in the Japanese Pharmacopoeia provided that an auxiliary disk was not used.

The measurements for the hardness and disintegration time were each repeated six times, and average values thereof were regarded as measurement results.

The dry material of the micro-fibrillated cellulose ("CELISH") was prepared in accordance with the method described in Example 3 of PTL 2.

EXAMPLES

Example 1

Production of Disintegrative Particulate Composition 1

340 g of mannitol (D-mannitol, Merck Ltd.), 40 g of dry material of micro-fibrillated cellulose ("CELISH FD-100G", Daicel FineChem Ltd.) and 20 g of crospovidone (Polyplasdone INF-10, ISP Japan) were mixed to obtain disintegrative particulate composition 1.

Production of Orally Disintegrating Tablet 1

99.5 parts by weight of the resulting disintegrative particulate composition 1 was mixed with 0.5 parts by weight of magnesium stearate (Taihei Chemical Industrial Co. Ltd.). The mixture was then subjected to tableting at a tablet compression force of 8 kN with a simple tableting machine (HANDTAB-100, ICHIHASHI-SEIKI Co., Ltd.) to thereby obtain an angled-corner flat tablet having a diameter of 8.0 mm and a weight of 250 mg.

Example 2

Production of Disintegrative Particulate Composition 2

340 g of mannitol (D-mannitol, Merck Ltd.), 40 g of dry material of micro-fibrillated cellulose ("CELISH FD-100G", Daicel FineChem Ltd.) and 20 g of starch sodium glycolate (Primojel, DMV-Fonterra Excipients GmBH&Co.) were mixed to obtain disintegrative particulate composition 2.

Production of Orally Disintegrating Tablet 2

The resulting disintegrative particulate composition 2 was subjected to tableting in the same manner as Example 1 to thereby obtain an angled-corner flat tablet having a diameter of 8.0 mm and a weight of 250 mg.

Example 3

Production of Disintegrative Particulate Composition 3

340 g of mannitol (D-mannitol, Merck Ltd.), 40 g of dry material of micro-fibrillated cellulose ("CELISH FD-100G", Daicel FineChem Ltd.), 20 g of starch sodium glycolate (Primojel, DMV-Fonterra Excipients GmBH&Co.) and 20 g of crystalline cellulose (CEOLUS PH-101, Asahi Kasei Chemicals Corp.) were mixed to obtain disintegrative particulate composition 3.

Production of Orally Disintegrating Tablet 3

The resulting disintegrative particulate composition 3 was subjected to tableting in the same manner as Example 1 to thereby obtain an angled-corner flat tablet having a diameter of 8.0 mm and a weight of 250 mg.

Comparative Example 1

380 g of mannitol (D-mannitol, Merck Ltd.) and 20 g of starch sodium glycolate (Primojel, DMV-Fonterra Excipients GmBH&Co.) were mixed.

The resulting mixture was subjected to tableting in the same manner as Example 1 to thereby obtain an angled-corner flat tablet having a diameter of 8.0 mm and a weight of 250 mg.

Comparative Example 2

380 g of mannitol (D-mannitol, Merck Ltd.), 20 g of starch sodium glycolate (Primojel, DMV-Fonterra Excipients GmBH&Co.) and 80 g of crystalline cellulose (CEOLUS PH-101, Asahi Kasei Chemicals Corp.) were mixed.

The resulting mixture was subjected to tableting in the same manner as Example 1 to thereby obtain an angled-corner flat tablet having a diameter of 8.0 mm and a weight of 250 mg.

Example 4

Production of Disintegrative Particulate Composition 4

As the first wet granulation step, 220 g of mannitol (D-mannitol, Merck Ltd.), 80 g of dry material of micro-fibrillated cellulose ("CELISH FD-100G", Daicel Fine-Chem Ltd.) and 80 g of crystalline cellulose (CEOLUS PH-101, Asahi Kasei Chemicals Corp.) were charged to a fluidized-bed granulator (FL-LABO, Freund Corporation), and 240 g of purified water was sprayed onto the resulting mixture at a rate of 12 g/minute to thereby granulate the mixture. Further, as the second wet granulation step, 20 g of crospovidone (Polyplasdone INF-10, ISP Japan) was added to the resulting granules, and 300 g of purified water was sprayed thereto at 10 g/minute to thereby obtain disintegrative particulate composition 4. The resulting disintegrative particulate composition 4 had the following values for physical properties: (1) an average particle size of 105 microns and (2) a water content of 1.8% by weight.

Production of Orally Disintegrating Tablet 4

0.5 parts by weight of magnesium stearate (Taihei Chemical Industrial Co. Ltd.) was added to 99.5 parts by weight of the disintegrative particulate composition 4 and mixed with each other. The mixture was then subjected to tableting at tablet compression forces of 6 and 8 kN with a simple tableting machine (HANDTAB-100, ICHIHASHI-SEIKI Co., Ltd.) to thereby obtain an angled-corner flat tablet having a diameter of 8.0 mm and a weight of 250 mg.

Example 5

Production of Disintegrative Particulate Composition 5

As the first wet granulation step, 220 g of mannitol (D-mannitol, Merck Ltd.), 80 g of dry material of micro-fibrillated cellulose ("CELISH FD-100G", Daicel Fine-Chem Ltd.) and 80 g of crystalline cellulose (CEOLUS PH-101, Asahi Kasei Chemicals Corp.) were charged to the fluidized-bed granulator (FL-LABO, Freund Corporation), and 240 g of purified water was sprayed onto the resulting mixture at a rate of 12 g/minute to thereby granulate the mixture. Further, as the second wet granulation step, 20 g of starch sodium glycolate (Primojel, DMV-Fonterra Excipients GmBH&Co.) was added to the resulting granules, and 300 g of purified water was sprayed thereto at 10 g/minute to thereby obtain disintegrative particulate composition 5. The resulting disintegrative particulate composition 5 had the following values for physical properties: (1) an average particle size of 84 microns and (2) a water content of 2.5% by weight.

Production of Orally Disintegrating Tablet 5

The resulting disintegrative particulate composition 5 was subjected to tableting in the same manner as Example 4 to thereby obtain an angled-corner flat tablet having a diameter of 8.0 mm and a weight of 250 mg.

Comparative Example 3

As the first wet granulation step, 300 g of mannitol (D-mannitol, Merck Ltd.) and 80 g of crystalline cellulose (CEOLUS PH-101, Asahi Kasei Chemicals Corp.) were charged to the fluidized-bed granulator (FL-LABO, Freund Corporation), and 240 g of purified water was sprayed onto the resulting mixture at a rate of 12 g/minute to thereby granulate the mixture. Further, as the second wet granulation step, 20 g of crospovidone (Polyplasdone INF-10, ISP Japan) was added to the resulting granules, and 300 g of purified water was sprayed thereto at 10 g/minute to thereby obtain granules. The resulting granules had the following values for physical properties: (1) an average particle size of 92 microns and (2) a water content of 1.4% by weight.

The resulting granules were subjected to tableting in the same manner as Example 4 to thereby obtain an angled-corner flat tablet having a diameter of 8.0 mm and a weight of 250 mg.

Comparative Example 4

As the first wet granulation step, 300 g of mannitol (D-mannitol, Merck Ltd.) and 80 g of crystalline cellulose (CEOLUS PH-101, Asahi Kasei Chemicals Corp.) were charged to the fluidized-bed granulator (FL-LABO, Freund Corporation), and 240 g of purified water was sprayed onto the resulting mixture at a rate of 12 g/minute to thereby granulate the mixture. Further, as the second wet granulation step, 20 g of starch sodium glycolate (Primojel, DMV-Fonterra Excipients GmBH&Co.) was added to the resulting granules, and 300 g of purified water was sprayed thereto at 10 g/minute to thereby obtain granules. The resulting granules had the following values for physical properties: (1) an average particle size of 110 microns and (2) a water content of 1.5% by weight.

The resulting granules were subjected to tableting in the same manner as Example 4 to thereby obtain an angled-corner flat tablet having a diameter of 8.0 mm and a weight of 250 mg.

Example 6

Production of Disintegrative Particulate Composition 6

270 g of mannitol (D-mannitol, Merck Ltd.), 80 g of corn starch (NIHON SHOKUHIN KAKO CO., LTD.) and 20 g of partially α-starch (PCS PC-10, Asahi Kasei Chemicals Corp.) were charged to the fluidized-bed granulator (FL-LABO, Freund Corporation), and 600 g of 5% suspension of wet material of micro-fibrillated cellulose ("CELISH FD-200L", Daicel FineChem Ltd.) in water was sprayed onto the resulting mixture at a rate of 12 g/minute, so that the mixture was granulated to thereby obtain disintegrative particulate composition 6. The resulting disintegrative particulate composition 6 had the following values for physical properties: (1) an average particle size of 135 microns and (2) a water content of 2.5% by weight.

Production of Orally Disintegrating Tablet 6

The resulting disintegrative particulate composition 6 was subjected to tableting in the same manner as Example 4 to thereby obtain an angled-corner flat tablet having a diameter of 8.0 mm and a weight of 250 mg.

Comparative Example 5

300 g of mannitol (D-mannitol, Merck Ltd.), 80 g of corn starch (NIHON SHOKUHIN KAKO CO., LTD.) and 20 g of partially α-starch (PCS PC-10, Asahi Kasei Chemicals Corp.) were charged to the fluidized-bed granulator (FL-LABO, Freund Corporation), and 600 g of purified water was sprayed onto the resulting mixture at a rate of 12 g/minute to thereby obtain granules. The resulting granules had the following values for physical properties: (1) an average particle size of 85 microns and (2) a water content of 2.1% by weight.

The resulting granules were subjected to tableting in the same manner as Example 4 to thereby obtain an angled-corner flat tablet having a diameter of 8.0 mm and a weight of 250 mg.

Evaluation of the Test of Hardness and Disintegration Time

The above Examples and Comparative Examples were measured with respect to their hardness and disintegration time based on the following conditions/methods. The test results of hardness and disintegration time are shown in Tables 1~3.

TABLE 1

| Orally Disintegrating Tablet | Ex. 1 | Ex. 2 | Ex. 3 | Comparative Example 1 | Comparative Example 2 |
|---|---|---|---|---|---|
| Tablet Compression Force (kN) | 8 | 8 | 8 | 8 | 8 |
| Tablet Hardness (N) | 75 | 75 | 103 | 20 | 50 |
| Disintegration Time in Water (s) | 19 | 19 | 15 | 24 | 22 |

TABLE 2

| Orally Disintegrating Tablet | Example 4 | | Example 5 | |
|---|---|---|---|---|
| Tablet Compression Force (kN) | 6 | 8 | 6 | 8 |
| Tablet Hardness (N) | 91 | 118 | 88 | 111 |
| Disintegration Time in Water (s) | 14 | 16 | 13 | 16 |

| Orally Disintegrating Tablet | Comparative Example 3 | | Comparative Example 4 | |
|---|---|---|---|---|
| Tablet Compression Force (kN) | 6 | 8 | 6 | 8 |
| Tablet Hardness (N) | 53 | 76 | 46 | 63 |
| Disintegration Time in Water (s) | 16 | 15 | 21 | 22 |

TABLE 3

| Orally Disintegrating Tablet | Example 6 | | Comparative Example 5 | |
|---|---|---|---|---|
| Tablet Compression Force (kN) | 6 | 8 | 6 | 8 |
| Tablet Hardness (N) | 52 | 71 | 21 | 34 |
| Disintegration Time in Water (s) | 17 | 25 | 29 | 33 |

The results shown in Table 1 demonstrate that the tablets produced by using the mixture comprising the dry material of "CELISH" (the disintegrative particulate composition according to the present invention) in Examples 1~3 have more excellent tablet hardness and disintegrability than the tablets not comprising the dry material of "CELISH" (Comparative Examples 1 and 2).

The results shown in Table 2 demonstrate that the tablets comprising the dry material of "CELISH" and produced by the two-stage wet granulation process consisting of the first and second wet granulation steps (the disintegrative particulate composition according to the present invention) in Examples 4 and 5 have more excellent tablet hardness and disintegrability, and more excellent formability that a higher tablet hardness is obtained with a lower tablet compression force, when compared to the tablets produced by the same process but not comprising the dry material of "CELISH" (Comparative Examples 3 and 4).

The results shown in Table 3 demonstrate that the tablets produced by the wet granulation process comprising the slurry of "CELISH" (the disintegrative particulate composition according to the present invention) in Example 6 has more excellent tablet hardness and disintegrability, and more excellent formability that a higher tablet hardness is obtained with a lower tablet compression force, when compared to the tablets produced by the same process using purified water (Comparative Example 5).

Examples 7~14: Production of Orally Disintegrating Tablet

The disintegrative particulate composition 5 in the Example 5, main medicinal ingredient listed in Table 4 and 0.5 parts by weight of magnesium stearate were mixed with each other. The mixture was then subjected to tableting at tablet compression forces described in Table 4 with a simple tableting machine (HANDTAB-100, ICHIHASHI-SEIKI Co., Ltd.) to thereby obtain an angled-corner flat tablet having a diameter of 8.0 mm and a weight of 250 mg.

Evaluation of the Test of Hardness and Disintegration Time

The tables obtained in Examples 7~14 were measured with respect to their hardness and disintegration time. The test results of hardness and disintegration time are shown in Table 4.

TABLE 4

| | Main Medicinal Ingredient | Content (%) | Tablet Compression Force (kN) | Tablet Hardness (N) | Disintegration Time in Water (s) |
|---|---|---|---|---|---|
| Ex.7 | Ascorbic | 40 | 10 | 61 | 20 |
| Ex.8 | Acid | 50 | 12 | 52 | 19 |
| Ex.9 | Caffeine | 40 | 4 | 57 | 11 |
| Ex.10 | | 60 | 4 | 60 | 10 |
| Ex.11 | | 70 | 4 | 65 | 14 |
| Ex.12 | β-carotene | 20 | 3 | 53 | 22 |
| Ex.13 | Ethenzamide | 40 | 6 | 65 | 14 |
| Ex.14 | | 60 | 6 | 71 | 19 |

Example 15

Production of Disintegrative Particulate Composition 7

270 g of lactose (SpheroLac, MEGGLE Co., LTd.), 80 g of corn starch (NIHON SHOKUHIN KAKO CO., LTD.) and 20 g of partially α-starch (PCS PC-10, Asahi Kasei Chemicals Corp.) were charged to the fluidized-bed granulator (FL-LABO, Freund Corporation), and 600 g of 5% suspension of wet material of micro-fibrillated cellulose ("CELISH FD200L", Daicel FineChem Ltd.) in water was sprayed onto the resulting mixture at a rate of 12 g/minute, so that the mixture was granulated to thereby obtain disintegrative particulate composition 7. The resulting disintegrative particulate composition 7 had the following values for physical properties: (1) an average particle size of 157 microns and (2) a water content of 2.4% by weight.

Production of Orally Disintegrating Tablet 15

The resulting disintegrative particulate composition 7 was subjected to tableting in the same manner as Example 4 but at tablet compression forces of 8 and 10 kN to thereby obtain an angled-corner flat tablet having a diameter of 8.0 mm and a weight of 250 mg.

Example 16

Production of Disintegrative Particulate Composition 8

270 g of erythritol (Erythritol T fine powder, MITUSBISHIKAGAKU FOODS CORPORATION), 80 g of corn starch (NIHON SHOKUHIN KAKO CO., LTD.) and 20 g of partially α-starch (PCS PC-10, Asahi Kasei Chemicals Corp.) were charged to the fluidized-bed granulator (FL-LABO, Freund Corporation), and 600 g of 5% suspension of wet material of micro-fibrillated cellulose ("CELISH FD200L", Daicel FineChem Ltd.) in water was sprayed onto the resulting mixture at a rate of 12 g/minute, so that the mixture was granulated to thereby obtain disintegrative particulate composition 8. The resulting disintegrative particulate composition 8 had the following values for physical properties: (1) an average particle size of 174 microns and (2) a water content of 2.8% by weight.

Production of Orally Disintegrating Tablet 16

The resulting disintegrative particulate composition 8 was subjected to tableting in the same manner as Example 4 but at tablet compression forces of 4 and 6 kN to thereby obtain an angled-corner flat tablet having a diameter of 8.0 mm and a weight of 250 mg.

Example 17

Production of Disintegrative Particulate Composition 9

270 g of trehalose (Trehalose P, HAYASHIBARA CO., LTD.), 80 g of corn starch (NIHON SHOKUHIN KAKO CO., LTD.) and 20 g of partially α-starch (PCS PC-10, Asahi Kasei Chemicals Corp.) were charged to the fluidized-bed granulator (FL-LABO, Freund Corporation), and 600 g of 5% suspension of wet material of micro-fibrillated cellulose ("CELISH FD200L", Daicel FineChem Ltd.) in water was sprayed onto the resulting mixture at a rate of 12 g/minute, so that the mixture was granulated to thereby obtain disintegrative particulate composition 9. The resulting disintegrative particulate composition 9 had the following values for physical properties: (1) an average particle size of 180 microns and (2) a water content of 6.6% by weight.

Production of Orally Disintegrating Tablet 17

The resulting disintegrative particulate composition 9 was subjected to tableting in the same manner as Example 4 to thereby obtain an angled-corner flat tablet having a diameter of 8.0 mm and a weight of 250 mg.

Example 18

Production of Disintegrative Particulate Composition 10

270 g of mannitol (D-mannitol, Merck Ltd.), 80 g of corn starch (NIHON SHOKUHIN KAKO CO., LTD.) and 20 g of L-HPC (LH-21, Shin-Etsu Chemical Co., Ltd) were charged to the fluidized-bed granulator (FL-LABO, Freund Corporation), and 600 g of 5% suspension of wet material of micro-fibrillated cellulose ("CELISH FD200L", Daicel FineChem Ltd.) in water was sprayed onto the resulting mixture at a rate of 12 g/minute, so that the mixture was granulated to thereby obtain disintegrative particulate composition 10. The resulting disintegrative particulate composition 10 had the following values for physical properties: (1) an average particle size of 135 microns and (2) a water content of 4.1% by weight.

[Production of Orally Disintegrating Tablet 18]

The resulting disintegrative particulate composition 10 was subjected to tableting in the same manner as Example 4 to thereby obtain an angled-corner flat tablet having a diameter of 8.0 mm and a weight of 250 mg.

Example 19

Production of Disintegrative Particulate Composition 11

270 g of mannitol (D-mannitol, Merck Ltd.), 80 g of corn starch (corn starch, NIHON SHOKUHIN KAKO CO., LTD.) and 20 g of carmellose calcium (ECG-505, NICHIRIN CHEMICAL INDUSTRIES, LTD) were charged to the fluidized-bed granulator (FL-LABO, Freund Corporation), and 600 g of 5% suspension of wet material of micro-fibrillated cellulose ("CELISH FD200L", Daicel FineChem Ltd.) in water was sprayed onto the resulting mixture at a rate of 12 g/minute, so that the mixture was granulated to thereby obtain disintegrative particulate composition 11. The resulting disintegrative particulate composition 11 had the following values for physical properties: (1) an average particle size of 137 microns and (2) a water content of 3.1% by weight.

Production of Orally Disintegrating Tablet 19

The resulting disintegrative particulate composition 11 was subjected to tableting in the same manner as Example 4 to thereby obtain an angled-corner flat tablet having a diameter of 8.0 mm and a weight of 250 mg.

Example 20

Production of Disintegrative Particulate Composition 12

270 g of mannitol (D-mannitol, Merck Ltd.), 80 g of potato starch (NS-P20, Sanwa Starch Co., Ltd.) and 20 g of partially α-starch (PCS PC-10, Asahi Kasei Chemicals Corp.) were charged to the fluidized-bed granulator (FL-LABO, Freund Corporation), and 600 g of 5% suspension of wet material of micro-fibrillated cellulose ("CELISH FD200L", Daicel FineChem Ltd.) in water was sprayed onto the resulting mixture at a rate of 12 g/minute, so that the mixture was granulated to thereby obtain disintegrative particulate composition 12. The resulting disintegrative particulate composition 12 had the following values for physical properties: (1) an average particle size of 146 microns and (2) a water content of 3.3% by weight.

Production of Orally Disintegrating Tablet 20

The resulting disintegrative particulate composition 12 was subjected to tableting in the same manner as Example 4 to thereby obtain an angled-corner flat tablet having a diameter of 8.0 mm and a weight of 250 mg.

Example 21

Production of Disintegrative Particulate Composition 13

270 g of mannitol (D-mannitol, Merck Ltd.), 80 g of hydroxypropyl starch (HPS-101W, Freund Corporation) and 20 g of partially α-starch (PCS PC-10, Asahi Kasci Chemicals Corp.) were charged to the fluidized-bed granulator (FL-LABO, Freund Corporation), and 600 g of 5% suspension of wet material of micro-fibrillated cellulose ("CELISH FD200L", Daicel FineChem Ltd.) in water was sprayed onto the resulting mixture at a rate of 12 g/minute, so that the mixture was granulated to thereby obtain disintegrative particulate composition 13. The resulting disintegrative particulate composition 13 had the following values for physical properties: (1) an average particle size of 143 microns and (2) a water content of 2.6% by weight.

Production of Orally Disintegrating Tablet 21

The resulting disintegrative particulate composition 13 was subjected to tableting in the same manner as Example 4 to thereby obtain an angled-corner flat tablet having a diameter of 8.0 mm and a weight of 250 mg.

Example 22

Production of Disintegrative Particulate Composition 14

330 g of mannitol (D-mannitol, Merck Ltd.), 20 g of powdered cellulose (KC Flock, NIPPON PAPER Chemicals CO., LTD) and 20 g of partially α-starch (PCS PC-10, Asahi Kasei Chemicals Corp.) were charged to the fluidized-bed granulator (FL-LABO, Freund Corporation), and 600 g of 5% suspension of wet material of micro-fibrillated cellulose ("CELISH FD200L", Daicel FineChem Ltd.) in water was sprayed onto the resulting mixture at a rate of 12 g/minute, so that the mixture was granulated to thereby obtain disintegrative particulate composition 14. The resulting disintegrative particulate composition 14 had the following values for physical properties: (1) an average particle size of 152 microns and (2) a water content of 1.3% by weight.

Production of Orally Disintegrating Tablet 22

The resulting disintegrative particulate composition 14 was subjected to tableting in the same manner as Example 4 to thereby obtain an angled-corner flat tablet having a diameter of 8.0 mm and a weight of 250 mg.

Example 23

Production of Disintegrative Particulate Composition 15

330 g of mannitol (D-mannitol, Merck Ltd.), 20 g of anhydrous calcium phosphate (Taihei Chemical Industrial Co. Ltd.) and 20 g of partially α-starch (PCS PC-10, Asahi Kasei Chemicals Corp.) were charged to the fluidized-bed granulator (FL-LABO, Freund Corporation), and 600 g of 5% suspension of wet material of micro-fibrillated cellulose ("CELISH FD200L", Daicel FineChem Ltd.) in water was sprayed onto the resulting mixture at a rate of 12 g/minute, so that the mixture was granulated to thereby obtain disintegrative particulate composition 15. The resulting disintegrative particulate composition 15 had the following values for physical properties: (1) an average particle size of 192 microns and (2) a water content of 2.1% by weight.

Production of Orally Disintegrating Tablet 23

The resulting disintegrative particulate composition 15 was subjected to tableting in the same manner as Example 4 to thereby obtain an angled-corner flat tablet having a diameter of 8.0 mm and a weight of 250 mg.

Example 24

Production of Disintegrative Particulate Composition 16

270 g of mannitol (D-mannitol, Merck Ltd.), 80 g of corn starch (NIHON SHOKUHIN KAKO CO., LTD.) and 20 g of partially α-starch (PCS PC-10, Asahi Kasei Chemicals Corp.) were charged to the fluidized-bed granulator (FL-LABO, Freund Corporation), and 600 g of 5% suspension of wet material of micro-fibrillated cellulose ("CELISH FD-100F", Daicel FineChem Ltd.) in water was sprayed onto the resulting mixture at a rate of 12 g/minute, so that the mixture was granulated to thereby obtain disintegrative particulate composition 16. The resulting disintegrative particulate composition 16 had the following values for physical properties: (1) an average particle size of 138 microns and (2) a water content of 2.3% by weight.

Production of Orally Disintegrating Tablet 24

The resulting disintegrative particulate composition 16 was subjected to tableting in the same manner as Example 4 to thereby obtain an angled-corner flat tablet having a diameter of 8.0 mm and a weight of 250 mg.

Example 25

Production of Disintegrative Particulate Composition 17

270 g of mannitol (D-mannitol, Merck Ltd.), 80 g of corn starch (NIHON SHOKUHIN KAKO CO., LTD.) and 20 g of partially α-starch (PCS PC-10, Asahi Kasei Chemicals Corp.) were charged to the fluidized-bed granulator (FL-LABO, Freund Corporation), and 600 g of 5% suspension of wet material of micro-fibrillated cellulose (3% viscosity: 500 mPa·s) produced by the method disclosed in A-2007-231438 in water was sprayed onto the resulting mixture at a rate of 12 g/minute, so that the mixture was granulated to thereby obtain disintegrative particulate composition 17. The resulting disintegrative particulate composition 17 had the following values for physical properties: (1) an average particle size of 157 microns and (2) a water content of 2.9% by weight.

Production of Orally Disintegrating Tablet 25

The resulting disintegrative particulate composition 17 was subjected to tableting in the same manner as Example 4 to thereby obtain an angled-corner flat tablet having a diameter of 8.0 mm and a weight of 250 mg.

Example 26

Production of Disintegrative Particulate Composition 18

270 g of mannitol (D-mannitol, Merck Ltd.), 80 g of corn starch (NIHON SHOKUHIN KAKO CO., LTD.) and 20 g of partially α-starch (PCS PC-10, Asahi Kasei Chemicals Corp.) were charged to a fluidized-bed granulator (FL-LABO, Freund Corporation), and 600 g of 5% suspension of wet material (2) of micro-fibrillated cellulose (5% viscosity: 2600 mPa·s) produced by the method disclosed in A-2007-231438 in water was sprayed onto the resulting mixture at a rate of 12 g/minute, so that the mixture was granulated to thereby obtain disintegrative particulate composition 18. The resulting disintegrative particulate composition 18 had the following values for physical properties: (1) an average particle size of 167 microns and (2) a water content of 2.7% by weight.

Production of Orally Disintegrating Tablet 26

The resulting disintegrative particulate composition 18 was subjected to tableting in the same manner as Example 4 to thereby obtain an angled-corner flat tablet having a diameter of 8.0 mm and a weight of 250 mg.

Evaluation of the Test of Hardness and Disintegration Time

The tables obtained in the above Examples were measured with respect to their hardness and disintegration time. The test results of hardness and disintegration time are shown in Table 5.

TABLE 5

| Orally Disintegrating Tablet | Example 15 | | Example 16 | |
|---|---|---|---|---|
| Tablet Compression Force (kN) | 8 | 10 | 4 | 6 |
| Tablet Hardness (N) | 49 | 60 | 91 | 122 |
| Disintegration Time in Water (s) | 12 | 12 | 22 | 34 |

| Orally Disintegrating Tablet | Example 17 | | Example 18 | |
|---|---|---|---|---|
| Tablet Compression Force (kN) | 4 | 6 | 6 | 8 |
| Tablet Hardness (N) | 51 | 74 | 85 | 106 |
| Disintegration Time in Water (s) | 24 | 28 | 20 | 21 |

TABLE 5-continued

| Orally Disintegrating Tablet | Example 19 | | Example 20 | |
| --- | --- | --- | --- | --- |
| Tablet Compression Force (kN) | 6 | 8 | 6 | 8 |
| Tablet Hardness (N) | 74 | 96 | 73 | 99 |
| Disintegration Time in Water (s) | 17 | 20 | 20 | 25 |

| Orally Disintegrating Tablet | Example 21 | | Example 22 | |
| --- | --- | --- | --- | --- |
| Tablet Compression Force (kN) | 6 | 8 | 6 | 8 |
| Tablet Hardness (N) | 68 | 89 | 82 | 101 |
| Disintegration Time in Water (s) | 22 | 30 | 26 | 35 |

| Orally Disintegrating Tablet | Example 23 | | Example 24 | |
| --- | --- | --- | --- | --- |
| Tablet Compression Force (kN) | 6 | 8 | | 8 |
| Tablet Hardness (N) | 74 | 103 | | 64 |
| Disintegration Time in Water (s) | 29 | 42 | | 39 |

| Orally Disintegrating Tablet | Example 25 | | Example 26 | |
| --- | --- | --- | --- | --- |
| Tablet Compression Force (kN) | 6 | 8 | 6 | 8 |
| Tablet Hardness (N) | 58 | 81 | 69 | 94 |
| Disintegration Time in Water (s) | 19 | 24 | 22 | 28 |

INDUSTRIAL APPLICABILITY

The present invention significantly contributes to research and development of orally-disintegrating tablets having excellent tablet hardness and disintegrability.

The invention claimed is:

1. A disintegrative particulate composition comprising a disintegrator component and micro-fibrillated cellulose,
wherein the micro-fibrillated cellulose is produced only by physical processing of natural cellulose, and
wherein an amount of the micro-fibrillated cellulose in the composition is in a range of 1% to 50% by dry weight.

2. The disintegrative particulate composition according to claim 1, wherein the micro-fibrillated cellulose has an average fiber length of 0.01-2 mm and an average fiber diameter of 0.001-1 µm.

3. The disintegrative particulate composition according to claim 1, wherein the disintegrator is one or more components selected from crospovidone, croscarmellose sodium, low substituted hydroxypropylcellulose, carboxymethylcellulose calcium, starch and processed starch.

4. The disintegrative particulate composition according to claim 3, wherein the starch is corn starch, potato starch, waxy corn starch, α-starch or partially α-starch, and the processed starch is starch sodium glycolate or hydroxypropyl starch.

5. The disintegrative particulate composition according claim 1, wherein the disintegrator is a water-insoluble polymer.

6. The disintegrative particulate composition according to claim 1, further comprising sugars or sugar alcohols.

7. The disintegrative particulate composition according to claim 1, further comprising an auxiliary excipient.

8. The disintegrative particulate composition according to claim 7, wherein the auxiliary excipient is a crystalline cellulose and/or powdered cellulose.

9. A disintegrating tablet for pharmaceuticals or foods, comprising the disintegrative particulate composition according to claim 1.

10. The disintegrating tablet according to claim 9, which has tablet hardness of from 20 to 200 N, and disintegration time in water of from 1 to 60 sec.

11. A disintegrating tablet comprising the disintegrative particulate composition according to claim 1.

12. The disintegrating tablet according to claim 9, which has tablet hardness of from 50 to 150 N, and disintegration time in water of from 1 to 30 sec.

13. The disintegrative particulate composition according to claim 1, wherein an amount of the disintegrator component in the composition is in a range of 1% to 30% by weight.

* * * * *